United States Patent [19]
Jackson et al.

[11] Patent Number: 5,668,479
[45] Date of Patent: Sep. 16, 1997

[54] MULTIPURPOSE SENSOR FOR BELT CONVEYOR

[75] Inventors: Samuel G. Jackson; S. Chris Jackson; Martin L. Mehner; John C. Fabian; Sadaf Khalil, all of Lubbock, Tex.; Mitesh Shah, Piscataway, N.J.

[73] Assignee: Jackson-Charter Limited Partnership, Lubbock, Tex.

[21] Appl. No.: 526,993

[22] Filed: Sep. 12, 1995

[51] Int. Cl.$^6$ .................................................. G01R 27/08
[52] U.S. Cl. ...................... 324/695; 324/696; 324/690; 324/701; 324/717
[58] Field of Search .................... 324/695, 696, 324/690, 689, 720, 701, 717

[56] References Cited

U.S. PATENT DOCUMENTS

| | | | |
|---|---|---|---|
| 2,653,298 | 9/1953 | McKinley | 324/695 |
| 3,114,613 | 12/1963 | Neitzel et al. | 34/48 |
| 3,141,129 | 7/1964 | Dietert | 324/695 |
| 3,296,524 | 1/1967 | Updegraff | 324/689 |
| 3,355,665 | 11/1967 | Fegan | 324/695 |
| 3,376,877 | 4/1968 | Fegan | 324/695 |
| 5,087,120 | 2/1992 | Anthony | 356/36 |
| 5,125,279 | 6/1992 | Anthony et al. | 73/866 |

*Primary Examiner*—Ernest F. Karlsen
*Assistant Examiner*—Jose M. Solis
*Attorney, Agent, or Firm*—Charles D. Gunter, Jr.

[57] ABSTRACT

Apparatus for measuring moisture content and bulk flow rate of cotton and other bulk materials, such as wool or wood chips, while they are being transported on a belt conveyor. The apparatus comprises resistance-sensing electrode fingers pendulously mounted over the conveyor, the movement of the resistance-sensing fingers being halted in their downward arcuate path by the sensed material. The weight of the electrode assembly presses the fingers against the material with uniform pressure. The angular displacement of the fingers about an axis of suspension is used as a measure of bulk flow rate.

14 Claims, 1 Drawing Sheet

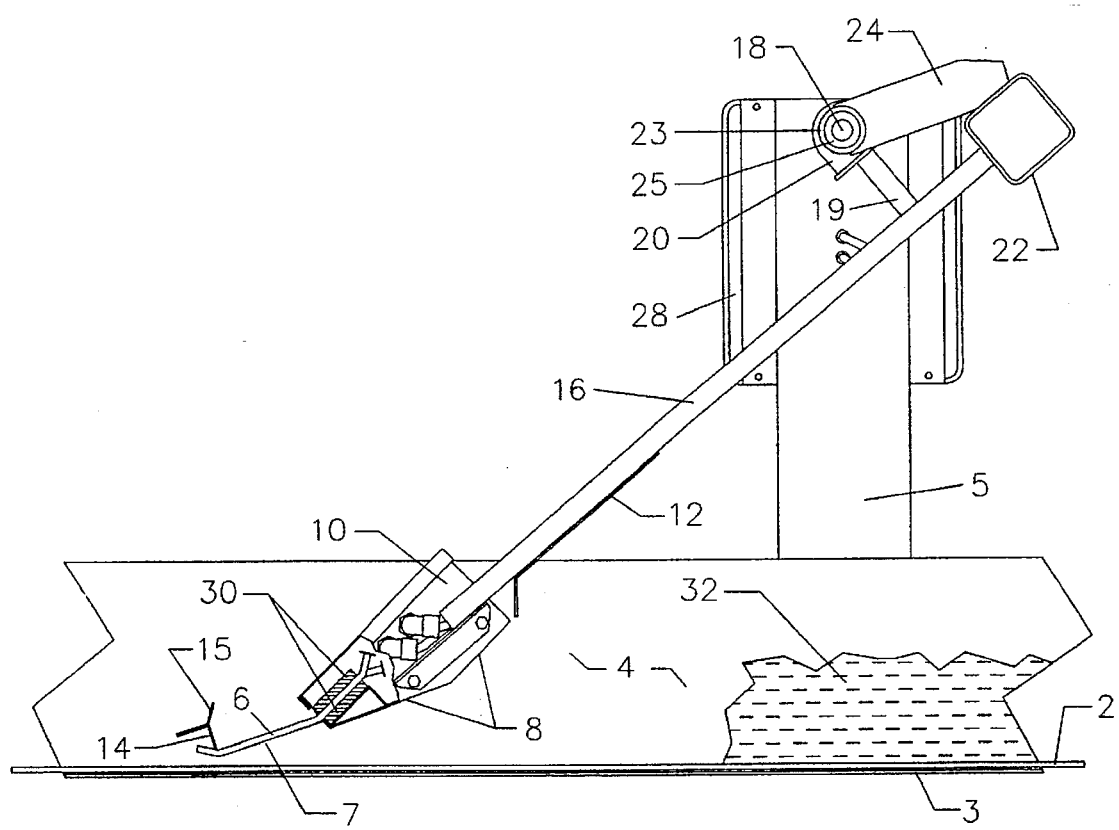
Fig. 1
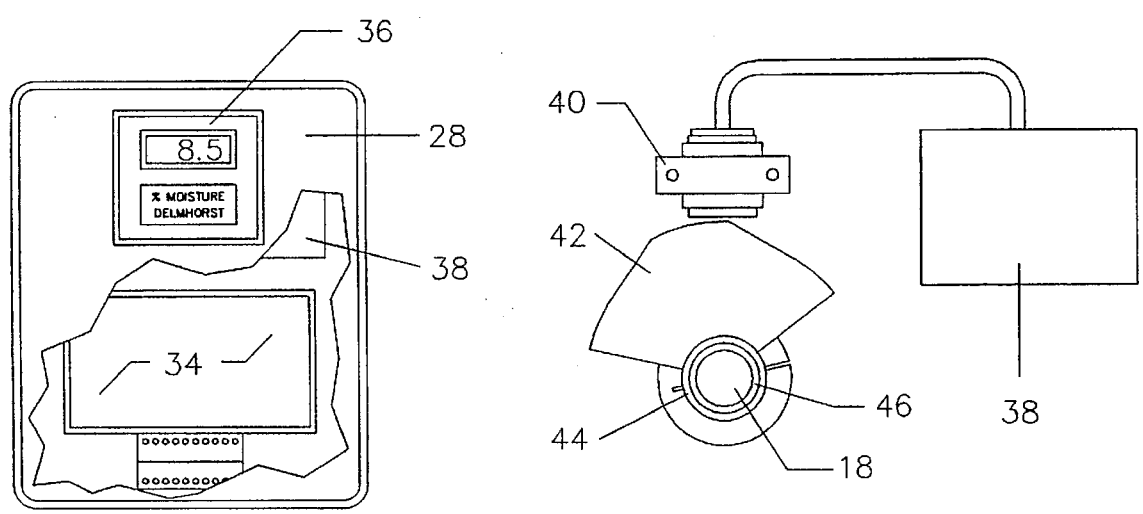
Fig. 2
Fig. 3

MULTIPURPOSE SENSOR FOR BELT CONVEYOR

BACKGROUND OF THE INVENTION

1. Field of the Invention

The present invention relates generally to an apparatus for measuring the moisture content of moving bulk material and, more specifically to an apparatus for measuring moisture content and bulk flow rate of cotton and other materials while they are being transported on a belt conveyor.

2. Description of the Prior Art

In processing cotton, its moisture content is always of critical importance. This is true whether an operator is drying cotton in order to preclean it in a cotton gin, preparing to measure the fiber properties of lint cotton at a classing office, or preparing to spin the cotton in a spinning mill.

The most popular method of measuring cotton moisture content is to measure its electrical resistance or its reciprocal, electrical conductivity. This method is reliable because the specific resistance of cotton fiber increases by a factor of about 5.5 for every one percent decrease in moisture content. The method is being used with good results on unprocessed seed cotton. Since such material has not been dried, the reading is indicative, not only of fiber moisture, but of the probable moisture level of the cottonseed.

The resistance method is particularly desirable for measuring after-drying moisture in seed cotton. The drying process dries the cotton fiber, which is still attached to the seeds, but has very little effect on the moisture content of the seeds. The resistance method in this case is highly selective, measuring lint moisture, the variable being affected, and ignoring an extraneous variable, seed moisture.

The resistance method is also adaptable to making continuous measurements on flowing streams of cotton, instead of taking intermittent samples. Certain precautions and conditions must be observed in utilizing this method, however, which have led to problems in the devices of the prior art.

It is important that the measuring electrode be pressed against the cotton with a uniform pressure. Variations in this pressure will give an apparent change in resistance which is not caused by a change in moisture content. If the cotton being analyzed is rather dry, another factor which must be considered is the generation of static electricity due to movement of the cotton, which may affect the accuracy of resistance readings.

It is common practice in textile mills and paper mills to utilize the resistance method to measure moisture in moving webs of material. The electrode is usually a roller type where the web is moving at a fast rate. For slower moving webs, electrodes which slide on the moving web are often used.

Samuel Jackson used the roller electrode method of measuring cotton moisture in a moving bed dryer in a cotton gin in Madison, Ala., in 1966. The control system modulated the temperature of the drying air to yield a constant final moisture content at the end of the dryer bed. It used a cylindrical drum about 12" diameter and 24" wide mounted on an axle which, in turn, rotated about a point well above the bed of cotton to accommodate varying depths of the cotton bed. When lack of cotton let the drum come within 1" of the moving steel dryer apron, a limit switch stopped all control action.

The electrode's cylindrical surface was covered with a copper-glass-epoxy etched electrode which was connected, through slip-rings, to the electronic measurement and control devices. The electrode had arrays of copper strips with about 10 mm of exposed insulation between each strip. Three such arrays were connected in series so contact by pieces of highly conductive trash would not drive the moisture reading entirely upscale. This control system was used for about 20 years.

Several prior art references are also known which teach methods of measuring the moisture content of seed cotton. One method of obtaining an accurate moisture reading of seed cotton coming into a cotton gin is described and claimed by Neitzel in U.S. Pat. No. 3,114,613. This involves using a pneumatic cylinder to compress seed cotton in a feed control bin against an electrode on the other side of the bin. This is not a continuous process, but depends on intermittently sampling the cotton. This apparatus did attempt to solve the problem of obtaining uniform pressure between the electrode and the cotton being analyzed. The use of a pneumatic cylinder to intermittently sample cotton by pressing a sample mass against a side wall was also the subject of U.S. Pat. No. 5,125,279, to Anthony.

In many modern cotton gins, the incoming seed cotton from the module feeder is conveyed by air directly into the gin's drying system. Only the small percentage of cotton which comes to the gin in trailers passes through a feed control bin, so the method described in the above-referenced patents cannot be used on the majority of the cotton being processed today. In order to solve this problem, Anthony describes an improved "paddle sampler" in his later issued U.S. Pat. No. 5,087,120. The "paddle sampler" intermittently gathers a sample of cotton from an airborne stream on a "paddle" which slowly rotates 180 degrees against the direction of flow. The paddle then presses the sample against a sensing electrode with constant pressure.

Unfortunately, this apparatus did not solve the problem of measuring seed cotton while it is being conveyed in hot air. The stream of hot air blasting against the sample while it is being gathered on the paddle dries it so much that the moisture measurement is not usable. Where the cotton is conveyed by ambient air, however, the paddle sampler method can be used to give accurate moisture readings. Since cotton is usually conveyed from the module feeder in a stream of hot air, a need existed to develop another method of measuring its moisture content.

Although designed for gathering cotton from a flowing air stream, the paddle sampler has been used with success in gathering samples of seed cotton from the enclosure of a module feeding disperser, where the disintegrated cotton is ballistically propelled. This still leaves the problem, however, that due to its location, it only measures moduled cotton and not trailer cotton.

Ordinary electrodes with no means of compression are widely used in feed control bins and in the hoppers above the extractor feeders in cotton gins. They have been successfully used on trailer cotton in the feed control bins. Since there is a wide range of moisture content in incoming cotton, the enhanced accuracy obtained by a compression device is not provided, however, in all cases. Fast input into the dryer control system for changes in moisture level is most important.

The use of compression apparatus is almost essential in the extractor feeder hoppers, where the range of moisture contents being measured is low and narrow, and greater precision is needed. Also, the drier cotton often has static charges which greatly distort the reading. Holding the sample against the electrode for some time allows static charges to dissipate before the reading is accepted.

It is accordingly an object of the present invention to provide an apparatus for making continuous moisture measurements on cotton or other material being transported by a belt conveyor which overcomes the above mentioned deficiencies of the prior art devices.

Another object of this invention is to provide an arrangement whereby uniform pressure is exerted on a sliding moisture sensing electrode.

Yet another object of this invention is to provide a sliding moisture electrode which is resistant to the disturbing influences of static electricity.

Another object of this invention is to provide an electrical signal which is directly proportional to the moisture content of the material being transported on a belt conveyor.

Yet another object of this invention is to provide a scalar electrical signal indicative of the bulk flow rate of the material transported on a belt conveyor, doing so with the same apparatus which measures moisture content.

Still another object of this invention is to provide those features described above, doing so with apparatus which is dependable in design, economical to manufacture and simple to install.

SUMMARY OF THE INVENTION

The apparatus of the invention is used to measure the moisture content of a bulk material moving along a path of travel. A housing is pivotally mounted over the path of travel of the moving bulk material. A plurality of conductive electrodes are carried by the pivotally mounted housing and are exposed at least partially therefrom for contacting the bulk material. Sensing means are provided for detecting an electrical resistance of the conductive electrodes, for converting the electrical resistance to an electrical signal which is proportional to the moisture content of the bulk material and for transmitting the electrical signal to a readout device.

Preferably, the apparatus is used for measuring the moisture content of cotton being transported on a belt conveyor. The housing is mounted over the belt conveyor for pivotal movement in an arcuate path which intersects the plane of the conveyor belt's path of travel. A plurality of rigid, resistance-sensing fingers are carried by the pivotally mounted housing and are exposed longitudinally at least partially therefrom for contacting the cotton being transported. The rigid, resistance-sensing fingers are disposed parallel to the direction of flow of the cotton on the conveyor belt, whereby the fingers make sliding contact with the cotton. Movement of the fingers is halted in their downward arcuate path by the cotton being sensed. The housing and fingers have a weight which presses the fingers against the cotton being sensed with a uniform pressure.

Preferably, the apparatus includes a mounting means for pivotally mounting the housing over the conveyor belt, the pivotal mounting means being so constructed that the rigid fingers exert adequate force on the conveyed cotton to provide an adequate measure of its specific resistance while allowing the apparatus to be compliant to the passage of the conveyed cotton.

The rigid fingers are preferably made up of at least two arrays of conductive fingers, the arrays being electrically connected in series. The rigid fingers which extend from the pivotally mounted housing have exposed surfaces, the exposed surfaces being coated with a thin layer of electrical insulation except for a portion of the exposed surfaces thereof which are intended to contact the conveyed cotton. The rigid fingers are supported within the housing by upper and lower insulating blocks and are also surrounded by a grounded shield. A grounded plate, carried by the pivotally mounted housing, wipes the conveyed cotton prior to its passage beneath the rigid fingers.

The apparatus can also include displacement means for measuring the vertical displacement of the housing and rigid conductive fingers above the path of travel. In those cases in which the displacement means is employed, the sensing means includes means for detecting an electrical resistance of the rigid conductive fingers and for detecting an angular position of the displacement means, for converting the electrical resistance and the angular displacement to electrical signals which are proportional to the moisture content and to the vertical displacement of the bulk material and for transmitting the electrical signals to a readout device. In this arrangement, the pivotal mounting means for pivotally mounting the housing over the path of travel includes a shaft which defines an axis of suspension, the housing being rotatable about the axis of suspension. The angular displacement of the rigid fingers about the axis of suspension is used as a measure of bulk flow rate of material being moved along the path of travel.

Additional objects, features and advantages will be apparent in the written description which follows.

BRIEF DESCRIPTION OF THE DRAWINGS

FIG. 1 is a transverse sectional view of the sensor of the present invention mounted on a belt conveyor trough;

FIG. 2 is a partially sectional view of the transmitter box of the apparatus of the invention; and FIG. 3 is a transverse sectional view of the portion of the displacement sensor assembly at the stationary shaft.

DETAILED DESCRIPTION OF THE INVENTION

All traveling-head module feeders and many stationary-head module feeders deliver the disintegrated seed cotton on a flat belt conveyor. This conveyor often delivers the stream of seed cotton into a "Hot Box" in which the seed cotton is picked up in hot air which drys it while conveying it into the cotton gin's drying system. A commercially available "Hot Box" is described in U.S. Pat. No. 4,817,295, issued Apr. 4, 1989, to Samuel G. Jackson. It is possible to place the separator and feed control bin used for trailer cotton above this same belt so both trailer and moduled cotton are delivered into the Hot Box. With this arrangement, the horsepower required to suck up the cotton out of the trailers and run the separator and feed bin is not used on moduled cotton.

In arrangements of this type, a need exists for measuring cotton moisture content on the conveyor belt just ahead of the Hot Box, in order to measure both trailer and moduled cotton. While roller electrodes have been used in the past, inherent mechanical problems and the necessity for using slip rings presented potential problems. Also, the incoming seed cotton is often wet and sticky, increasing the likelihood that it would adhere to the rolling electrode. Any wiper used to clean the electrode would be likely to affect the accuracy of its reading.

One approach to the problem was to use an electrode to slide on the surface of the cotton so the moving cotton would keep it clean. However, early attempts with this approach were not successful because the friction of the moving cotton wiping the polyethylene insulation between the electrodes generated tremendous static charges, which in some cases destroyed the measuring device.

In order to overcome these deficiencies, a floating sensor assembly was devised with a grounded stainless steel bottom surface which first pressed against and wiped the moving seed cotton to dissipate the static charges already in the cotton. Rigid steel electrode bars then contacted the moving cotton. These bars had only air between them at the area of contact with the cotton. They were clamped between grooved polyethylene insulator blocks which did not contact or rub against the moving cotton.

This apparatus worked well with one exception. In the region near the plastic clamping blocks, wet particles flipped up from the moving stream of cotton below and accumulated on the insulator blocks. This accumulation shorted the electrode bars, making the resistance readings higher than they should have been. This problem was overcome by coating the bars with a thin, hard insulating material, such as an epoxy, before assembly so accumulation of cotton on the bars or insulators would not affect the readings. The insulation was buffed off of the lower faces of the square electrode bars where they contact the moving cotton. In this way, only a negligible amount of insulation is exposed to wiping action against the moving cotton.

In addition to the anti-static wiping plate, both arrays of electrode fingers utilized in the present invention are surrounded with grounded stainless strips to shield them from static fields in the cotton passing on either side of the sensor assembly.

The floating sensor shown and described in the detailed description which follows utilizes a single pivot about which the sensor assembly rotates on bearings. While the sensor assembly could have been suspended on multiple pivot arms, or even on chains, so as to maintain a constant electrode attitude as it is pushed forward and upward by the moving material, the linkage assembly described herein was chosen for its simplicity. As used in the specification and claims, the phrase "pivotally mounted" is meant to include all such possibilities.

Most of our language in the present specifications is illustrative of the experience gained in measuring moisture in seed cotton in cotton gins. However, as will be apparent to those skilled in the art, the present invention is directly applicable to other fields, such as, but not limited to, measuring moisture content and bulk flow rate in wood chips, fibers and other granular or flowable solids or particulates. It is also capable of measuring moisture content in cotton lint samples in open trays. The descriptive terminology which follows should be taken in this broad context.

Another feature of this invention is the displacement sensing means which measures the vertical displacement of the bulk material being conveyed. As the pivoted moisture sensor is pushed upward by the mass of moving cotton, it rotates a steel cam in front of an analog proximity sensor. This sensor produces a 4 to 20 mA DC signal which is directly proportional to the thickness of the bed of cotton passing under the moisture sensor. This reading provides a reliable indication of the mass flow rate of the conveyed cotton. A signal of this type can be used in an appropriate control loop to maintain the desired flow rate of seed cotton into the gin.

Referring now to FIG. 1 of the drawings, an apparatus of the invention is shown for measuring the moisture content of a bulk material, such as cotton, moving along a path of travel. In this case, the path of travel is a conveyor belt 2 which slides along the conveyor trough floor 3. The upright supports 5 of the sensor apparatus are bolted to the upper flanges of the trough side 4. The apparatus is preferably extensible in width to accommodate troughs of various widths. A housing or box 10 is pivotally mounted over the path of travel of the moving bulk material. A plurality of conductive electrodes, such as rigid resistance-sensing fingers 6 are carried by the housing 10 and are exposed longitudinally at least partially therefrom for contacting the bulk material. By "exposed longitudinally" is meant that the electrode bars or fingers 6 have lower ends which extend lengthwise from the box 10 parallel to the direction of travel of the material on the conveyor, the fingers having upper ends which are clamped rigidly between grooved polyethylene insulator blocks 30. In the embodiment illustrated in FIG. 1, approximately two thirds of the overall length of the fingers 6 is exposed from the housing 10. The conveyed material 32 moves in the direction shown and is dragged under the sensor assembly by the moving belt. The material is deflected under the box 10 by an angled sheet 12 which prevents material from accumulating on the upper surface of the box 10. As it passes under the box, the material is wiped by the smooth, grounded stainless plate 8, which forms the bottom of the box 10.

The individual electrode fingers 6 must be large in cross section to have enough rigidity to maintain their position outside the box with no support. The fingers 6, shown in the drawing, are stainless steel square bars which are 8 mm square. The exposed surfaces of the electrode bars are first completely coated with a thin hard insulating material such as epoxy. This prevents shorting of the electrode by accumulations of material on top of the bars or on the insulator blocks 30. A lower portion 7 of the exposed surfaces of the fingers 6 which contact the moving cotton are buffed so that they will have good electrical contact with the cotton. The longitudinal shape of the electrode finger 6 and the orientation of the fingers is such that material which might be lodged between or above them will be removed by the wiping action of the moving material.

Preferably two arrays of electrode fingers are connected in series so that pieces of highly conductive trash contacting one array will not drive the moisture reading entirely upscale. Each array preferably has two or more electrode fingers 6 arranged side-by-side in a common plane. Because the specific resistance of cotton fiber increases in a highly factored relationship, shorting one of the arrays increases the moisture reading only about 0.4 percent.

A static shield 14 completely surrounds the two arrays of electrode bars. The cross-piece 15, which is at the downstream end of the electrode fingers, is elevated above the moving material and is shaped to discourage the capture of material. The box or housing 10 also serves to protect the connection ends of the electrode bars from foreign matter which might short them.

Although the preferred embodiment illustrated shows the electrical connections to the rigid conductive fingers and the clamping blocks supporting the fingers enclosed in the housing 10, it should be understood that housing 10 would not be necessary if the upper ends of the fingers and their electrical connections were to be embedded in a solid block of insulating material.

A mounting means is also provided for pivotally mounting the housing or box 10 over the conveyor belt 2. The mounting means is so constructed that the rigid fingers 6 exert adequate force on the conveyed material to provide an adequate measure of its specific resistance while allowing the apparatus to be compliant to the passage of the conveyed material.

Thus, the rotatable portion of the sensor assembly pivots about stationary shafts 18, which are welded to the upright supports 5. Two ball bearing pillow blocks 20 are connected to the support arms 16 by bearing supports 19. Two wires from the electrode assembly leave box 10 and run up one of the support arms 16, which are made of rectangular steel tubing. The wires leave the support arm near the bearing support 19, passing through holes in the upright support 5 and entering the transmitter box 28. The box may be mounted on either side of the conveyor trough for convenience of installation and operation.

At the upper end of support arms 16 is a transverse section of 4-inch square steel tubing with its ends welded shut, forming counterweight box 22. The counterweight box 22 serves to balance the rotating assembly to make the force applied by the electrode fingers large enough to give a reliable reading, yet not be so large as to impede the flow of material on the conveyor belt. To lessen the contact force of the electrode fingers, sand can be added to counterweight box 22.

The inwardly extending ends of the stationary shafts 18 are enclosed in a clamping tube 23. This clamping of the shafts rigidizes the entire support assembly and immobilizes the clamping tube. The clamping action is done by two Trantorque keyless bushings 25, one at each end of the tube. Clamping tube 23 has welded to it an adjustable stop 24, which restricts the downward travel of the rotating assembly by contacting the counterweight box 22. Clamping the ends of tube 23 not only allows adjustment of the support assembly for troughs of different width, but allows adjustment of stop 24 so the electrode bars 6 clear the conveyor belt when no material is present.

A sensing means is also provided for detecting an electrical resistance of the conductive electrode fingers 6, for converting the electrical resistance to an electrical signal which is proportional to the moisture content of the bulk material and for transmitting the electrical signal to a readout device. Referring to FIG. 2, the sensing means comprises a signal transmitter box 28 which contains the moisture transmitter 34, which is commercially available and manufactured for use in the present apparatus by Delmhorst Instrument Co of Towaco, N.J. It is powered by 24 volts DC, supplied from the central control facility. The circuitry in the transmitter utilizes the resistance from the two electrode wires to produce an output signal on two other wires corresponding to moisture content.

The output current ranges from 4 to 20 mA DC in such manner that the current is 4 mA when the electrode resistance corresponds to the lowest value of moisture content, usually 4%. The output is 20 mA when the resistance corresponds to the maximum moisture content, 16 or 18%. While the relationship of moisture content to resistance is highly nonlinear, the signal from the transmitter has been digitally characterized to be linear with respect to moisture content over its entire range. This means that the signal can be readily utilized by general purpose digital controllers or programmable controllers for use in automatic control procedures without further linearization. The moisture content and diagnostic messages appear on the readout device, in this case digital moisture display 36, mounted on the front of box 28.

The apparatus of the invention can also include an optional proximity sensor which serves as a displacement means for measuring the vertical displacement of the housing 10 and rigid fingers 6 above the path of travel of the bulk material being conveyed. The optional proximity transmitter 38 may be installed within the transmitter box 28. It is powered by the same 24 V DC supply and uses two other wires to deliver a 4 to 20 mA DC signal corresponding to the vertical displacement of the sensor assembly. Since these wires all carry DC, they can be run in one conduit without mutual interference of the various signals.

Referring to FIG. 3, the displacement means is further described. The cam tube 44 slips over one of the stationary shafts 18, and is fastened to one of the bearing supports 19 so that it rotates with the sensor assembly. A steel cam 42 is fastened to the cam tube 44 in such manner that its angular relationship to the cam tube is adjustable. Sleeve bearings 46 allow the cam assembly to rotate freely on shaft 18. As the cam rotates in front of the proximity sensor 40, the clearance between the cam and the sensor changes from 2 to 10 mm. This causes the signal produced by the analog proximity transmitter 38 to go from 4 to 20 mA. The cam is shaped so the relationship of the output current to vertical displacement is linear. It is symmetrical so it can be used on either side of the support assembly. The proximity transmitter 38 and sensor 40 are standard devices which are commercially available, in this case from Omron Electronics.

An invention has been provided with several advantages. The apparatus of the present invention provides continuous moisture measurements on cotton or other material being transported on a belt conveyor. The mounting arrangement which is utilized provides uniform pressure on the sliding moisture sensing electrodes. The electrodes which are utilized are designed to be resistant to static electricity in the environment. The sensing means of the invention provides electrical signals which are proportional to the moisture content of the material being transported and which are also indicative of the bulk flow rate of the material moving on the belt conveyor. The apparatus is simple in design and economical to manufacture and has relatively few moving parts which would require repair or replacement.

While the invention has been shown in only one of its forms, it is not thus limited but is susceptible to various changes and modifications without departing from the spirit thereof.

What is claimed is:

1. An apparatus for measuring the moisture content of a bulk material moving along a path of travel, the apparatus comprising:

a housing pivotally mounted over the path of travel of the moving bulk material;

a plurality of rigid conductive fingers carried by the pivotally mounted housing and exposed at least partially therefrom for contacting the bulk material, the rigid conductive fingers being disposed parallel to the direction of flow of the moving bulk material, whereby the fingers make sliding contact with the bulk material being moved;

displacement means for measuring the vertical displacement of the housing and rigid conductive fingers above the path of travel;

sensing means for detecting an electrical resistance of the rigid conductive fingers and for detecting an angular position of the displacement means, for converting the electrical resistance and the angular displacement electrical signals which are proportional to the moisture content and to the vertical displacement of the bulk material and for transmitting the electrical signals to a readout device.

2. An apparatus for measuring the moisture content of a bulk fibrous material moving along a path of travel, the apparatus comprising:

an assembly pivotally mounted over the path of travel of the moving bulk fibrous material, the assembly comprising:

a. a plurality of rigid conductive fingers, each finger having an exposed portion for contacting the bulk fibrous material, the exposed portions each having a lower end and having an oppositely arranged upper end which carries an electrical connection;

b. each of the rigid conductive fingers having a thin coating of electrical insulation on the exposed portions thereof except for a lower surface of each of the exposed portions which is intended to contact the moving material, the conductive fingers being separated only by air at the lower surfaces thereof where the fingers contact the conveyed material;

c. insulating and clamping means for maintaining the rigid conductive fingers in parallel arrangement to each other and in parallel disposition to the direction of flow of the moving bulk fibrous material, as the fingers make sliding contact with the bulk fibrous material being moved, the insulating and clamping means being shielded from the conveyed material to thereby prevent the insulating and clamping means from being rubbed by the conveyed material;

d. protective means for preventing contamination of or damage to the electrical connections to the rigid conductive fingers;

sensing means for detecting an electrical resistance of the conductive fingers, for converting the electrical resistance to an electrical signal which is a function of the moisture content of the bulk fibrous material and for transmitting the electrical signal to a readout device.

3. An apparatus for measuring the moisture content of cotton being transported on a belt conveyor, the apparatus comprising:

a housing mounted over the belt conveyor for pivotal movement in an arcuate path which intersects the plane of the conveyor belt;

a plurality of rigid, resistance-sensing fingers carried by the pivotally mounted housing, each finger having an exposed portion for contacting the cotton being transported, a lower end and an oppositely arranged upper end, the rigid, resistance-sensing fingers being disposed parallel to the direction of flow of the cotton on the conveyor belt, whereby the fingers make sliding contact with the cotton, movement of the fingers being halted in their downward arcuate path by the cotton being sensed, and wherein the housing and fingers have a weight which presses the fingers against the cotton being sensed with a uniform pressure, and wherein the rigid fingers each have their exposed portions coated with a thin layer of electrical insulation, except for a lower surface of each of the exposed portions which is intended to contact the cotton, the rigid fingers being separated only by air at the lower surfaces thereof where the fingers contact the cotton;

sensing means for detecting an electrical resistance of the rigid fingers, for converting the electrical resistance to an electrical signal which is a function of the moisture content of the cotton being transported and for transmitting the electrical signal to a readout device.

4. The apparatus of claim 3, wherein the rigid fingers are supported within the housing by upper and lower insulating blocks, and wherein the insulating blocks are shielded from cotton being conveyed, whereby the insulating blocks supporting the rigid fingers are not wiped against the conveyed cotton.

5. The apparatus of claim 4 in which the fingers are disposed in such manner that the flow of conveyed cotton will clean the fingers of accumulations of cotton.

6. The apparatus of claim 4 in which the rigid fingers are made up of at least two arrays of conductive fingers, the arrays being electrically connected in series.

7. The apparatus of claim 4, wherein the rigid fingers are surrounded by a grounded shield.

8. The apparatus of claim 7, wherein the grounded shield includes a grounded plate carried by the pivotally mounted housing, the grounded plate being arranged to wipe the conveyed cotton prior to its passage beneath the rigid fingers.

9. The apparatus of claim 2, wherein the rigid fingers are surrounded by a grounded shield.

10. The apparatus of claim 9, wherein the grounded shield includes a grounded plate carried by the pivotally mounted housing, the grounded plate being arranged to wipe the conveyed material prior to its passage beneath the rigid fingers.

11. The apparatus of claim 2 in which the protective means is a housing enclosing both the electrical connections and the insulating and clamping means.

12. The apparatus of claim 11 wherein the insulating and clamping means supporting the rigid fingers comprise upper and lower insulating blocks within the housing.

13. The apparatus of claim 1, further comprising:

pivotal mounting means for pivotally mounting the housing over the path of travel, the pivotal mounting means including a shaft which defines an axis of suspension, the housing being rotatable about the axis of suspension, whereby the rigid fingers exert adequate force on the conveyed material to provide an adequate measure of its specific resistance while allowing the apparatus to be compliant to the passage of the conveyed material.

14. The apparatus of claim 1, wherein the angular displacement of the rigid fingers about the axis of suspension is used as a measure of bulk flow rate of material being moved along the path of travel.

* * * * *